US011268921B2

(12) United States Patent
Steele et al.

(10) Patent No.: US 11,268,921 B2
(45) Date of Patent: Mar. 8, 2022

(54) DETERMINING MATERIAL COMPOSITION OF COOKWARE IN INDUCTION HEATING SYSTEMS

(71) Applicant: Haier US Appliance Solutions, Inc., Wilmington, DE (US)

(72) Inventors: Victoria Steele, Louisville, KY (US); Juliette Marie Dubon, Miami Lakes, FL (US); Michael Blum, Louisville, KY (US); Eric Scott Johnson, Louisville, KY (US)

(73) Assignee: Haier US Appliance Solutions, Inc., Wilmington, DE (US)

( * ) Notice: Subject to any disclaimer, the term of this patent is extended or adjusted under 35 U.S.C. 154(b) by 366 days.

(21) Appl. No.: 16/531,768

(22) Filed: Aug. 5, 2019

(65) Prior Publication Data
US 2021/0041384 A1  Feb. 11, 2021

(51) Int. Cl.
*G01R 27/28* (2006.01)
*G01N 27/02* (2006.01)
*G01N 33/20* (2019.01)
*H05B 6/12* (2006.01)
*G01R 19/00* (2006.01)
(Continued)

(52) U.S. Cl.
CPC ......... *G01N 27/025* (2013.01); *G01N 27/028* (2013.01); *G01N 33/20* (2013.01); *G01R 15/181* (2013.01); *G01R 19/0092* (2013.01); *G01R 27/2611* (2013.01); *G01R 29/0814* (2013.01); *H05B 6/1209* (2013.01); *B29C 65/483* (2013.01); *B29C 65/4835* (2013.01); *B29C 66/71* (2013.01); *B29C 66/7212* (2013.01)

(58) Field of Classification Search
CPC ............ G01R 27/2611; G01R 19/0092; G01R 15/181; G01R 29/0814; B29C 66/7212; B29C 66/71; B29C 65/483; B29C 65/4835; G01N 27/025; G01N 27/028; G01N 33/20; H05B 6/1209; H05B 2213/05; H05B 6/062
USPC ........... 324/76.11–76.83, 459, 600, 649, 654
See application file for complete search history.

(56) References Cited

U.S. PATENT DOCUMENTS 9,035,223 B2  5/2015  Noguchi et al.
9,247,588 B2  1/2016  Baarman et al.
(Continued)

FOREIGN PATENT DOCUMENTS

JP   2010108796 A   5/2010
JP   5089728 B2    12/2012
JP   5495960 B2    5/2014

*Primary Examiner* — Raul J Rios Russo
(74) *Attorney, Agent, or Firm* — Dority & Manning, P.A.

(57) ABSTRACT

Induction cooktops and operational methods are provided herein. A method of determining material composition of cookware on an induction cooktop can include determining that a piece of cookware is on the induction cooktop, inducing a current within the piece of cookware with an induction coil of the induction cooktop, and obtaining a peak induction coil current, a smoothed input line current, and a phase shift of current flowing in the induction coil. The method can further include comparing the peak induction coil current, the smoothed input line current, and the phase shift each to a set of predetermined ranges, and determining candidate material compositions for the cookware based on the comparing of each of the peak induction coil current, the smoothed input line current, and the phase shift.

20 Claims, 5 Drawing Sheets

(51) Int. Cl.
    *G01R 27/26*     (2006.01)
    *G01R 15/18*     (2006.01)
    *G01R 29/08*     (2006.01)
    *B29C 65/00*     (2006.01)
    *B29C 65/48*     (2006.01)

(56) References Cited

U.S. PATENT DOCUMENTS

| | | | |
|---|---|---|---|
| 9,826,576 B2 | 11/2017 | Yoshino et al. | |
| 2018/0176998 A1* | 6/2018 | Nam | H05B 6/1236 |
| 2019/0289678 A1* | 9/2019 | Nam | H05B 6/062 |
| 2021/0029787 A1* | 1/2021 | Nam | H05B 6/062 |

* cited by examiner

DETERMINING MATERIAL COMPOSITION OF COOKWARE IN INDUCTION HEATING SYSTEMS

FIELD OF THE INVENTION

The present subject matter relates generally to induction heating systems used, for instance, in induction cooktop appliances, and more particularly to determining material composition of cookware in induction heating systems and appliances.

BACKGROUND OF THE INVENTION

Induction cook-tops heat conductive cookware by magnetic induction. An induction cook-top applies radio frequency current to a heating coil to generate a strong radio frequency magnetic field on the heating coil. When a conductive vessel, such as a pan, is placed over the heating coil, the magnetic field coupling from the heating coil generates eddy currents on the vessel. This causes the vessel to heat.

An induction cook-top will generally heat any vessel of suitable conductive material of any size that is placed on the induction cook-top. Since the magnetic field is not visible, unless some secondary indicator is provided, it is not readily apparent whether the induction cook-top is powered (on) or off. Thus, it is possible for items placed, on the induction cook-top to be heated unintentionally, which could damage such items and create other problems.

There are multiple methods of vessel or pan detection on an induction cook-top. Some of these include mechanical switching, current detection, phase detection, optical sensing, and harmonic distortion sensing. In pan sensing methods that utilize phase detection and amplitude measurements, a current transformer can be used. When the system is operating at resonance, the optimal power transfer between the heating coil and the vessel will occur. However, resonance is dependent upon the load presented by the vessel. Furthermore, actual temperature of the cookware is also dependent upon composition of the vessel. Therefore, it may be desirable to be able to determine material composition of cookware in induction heating systems and appliances.

BRIEF DESCRIPTION OF THE INVENTION

Aspects and advantages of the invention will be set forth in part in the following description, or may be obvious from the description, or may be learned through practice of the invention.

In one example aspect of the present disclosure, a method of determining material composition of cookware on an induction cooktop is provided. The method can include determining that a piece of cookware is on the induction cooktop, inducing a current within the piece of cookware with an induction coil of the induction cooktop, and obtaining a peak induction coil current, a smoothed input line current, and a phase shift of current flowing in the induction coil. The method can further include comparing the peak induction coil current, the smoothed input line current, and the phase shift each to a set of predetermined ranges, and determining candidate material compositions for the cookware based on the comparing of each of the peak induction coil current, the smoothed input line current, and the phase shift.

According to another example aspect of the present disclosure, an induction cooktop is provided. The induction cooktop can include an induction coil, a switching device configured to operate the induction coil, and a controller configured to operate the switching device. The controller is configured to perform operations, the operations include determining that a piece of cookware is on the induction cooktop, inducing a current within the piece of cookware with an induction coil of the induction cooktop, and obtaining a peak induction coil current, a smoothed input line current, and a phase shift of current flowing in the induction coil. The method can further include comparing the peak induction coil current, the smoothed input line current, and the phase shift each to a set of predetermined ranges, and determining candidate material compositions for the cookware based on the comparing of each of the peak induction coil current, the smoothed input line current, and the phase shift.

According to yet another example aspect of the present disclosure, another method of determining material composition of cookware on an induction cooktop is provided. The method can include determining that a piece of cookware is on the induction cooktop, inducing a current within the piece of cookware with an induction coil of the induction cooktop, and obtaining a peak induction coil current, a smoothed input line current, and a phase shift of current flowing in the induction coil. The method can also include classifying the cookware as a candidate material based on a material composition class most common among k nearest neighbors of a database of values for the peak induction coil current, the smoothed input line current, and the phase shift, and determining that the material composition of the cookware is a particular material composition based on the classifying.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

DETAILED DESCRIPTION

Figure 1:
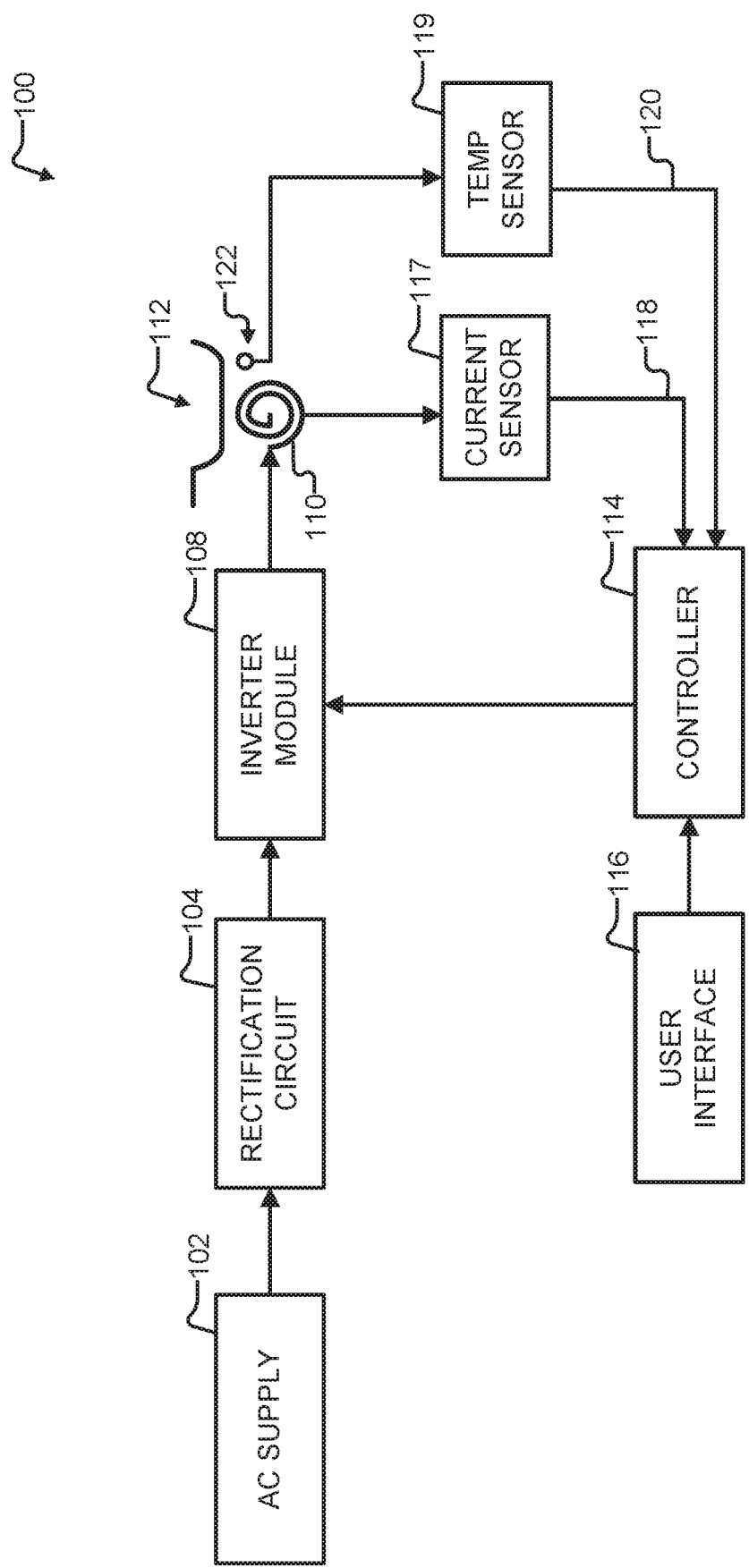
FIG. 1 shows a schematic block diagram of an induction heating system, according to example embodiments of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the term "or" is generally intended to be inclusive (i.e., "A or B" is intended to mean "A or B or both"). Furthermore, as used herein, terms of approximation, such as "approximately" or "substantially," refer to being within a ten percent margin of error.

As described herein, methods of determining the material composition of cookware placed on induction cooktops are provided. The methods may include determining a number of candidate material compositions using a controller. Subsequently, an actual material composition is chosen based on the candidate material compositions. Based on the actual material composition, accurate and precise cooking may be implemented using a temperature sensor. Temperature feedback provided by the sensor may be offset depending upon the material composition of the cookware, thereby more accurately reflecting the actual temperature of the cookware. Accordingly, example embodiments of the present disclosure benefit consumers by providing more precise cooking, save energy by providing for accurate heating profiles based on material composition of cookware, and provide for accurate temperature feedback to reduce the chance of damaging cookware due to overheating or overly aggressive heating profiles.

Furthermore, according to example aspects, material composition can be determined by comparing a peak induction coil current, a smoothed input line current, and a phase shift each to a set of predetermined ranges. This can provide for a more efficient determination of material composition. In this regard, computing resources can be reserved for more core functions of the controller.

Turning to the drawings, FIG. 1 is a schematic block diagram of an induction heating system 100 of an induction cooktop, according to one embodiment of the present disclosure. In operation, the system 100 can be configured to detect a presence of a vessel or cookware 112 on an induction coil 110 and control the power supplied to the induction coil 110 at a power level selected by a user from a range of user selectable power settings, where the power supplied is based on size and type of cookware detected and a selected power setting.

As shown schematically in FIG. 1, the induction heating system 100 generally includes AC supply 102, which may provide conventional 60 Hz 120 or 240 volt AC supplied by utility companies, and a conventional rectifier circuit 104 for rectifying the power signal from AC supply 102. Rectifier circuit 104 may include filter and power factor correction circuitry to filter the rectified voltage signal. The induction heating system 100 also includes an inverter module 108 for supplying an alternating current to the induction coil 110. Accordingly, the inverter module 108 may also be termed a variable frequency inverter module. The induction coil 110, when supplied by the inverter module 108 with an alternating current, inductively heats the cookware 112 or other object placed on, over, or near the induction coil 110. It will be understood that use of the term "cookware" herein is merely exemplary, and that term will generally include any object of a suitable type that is capable of being heated by an induction coil.

The frequency of the current supplied to the induction coil 110 by inverter module 108 and hence the output power of the induction coil 110 is controlled by controller 114 which controls the switching frequency of the inverter module 108 and one or more switching devices of the inverter module 108. The controller 114 may also be implemented as a microcontroller and/or gate driver to drive individual transistors or switching devices of the system 100 with pulse-width modulated signals.

A user interface 116 allows a user to establish the power output of the induction coil 110 by selecting a power setting from a plurality of user selectable settings. The user interface 116 may also provide for a user selection of a "precision cooking" mode or other suitable cooking mode whereby precise temperature control of the cookware 112 is possible due to determination of the material composition of the cookware 112. The user interface 116 is operatively connected to controller 114.

A current sensor 117 senses the current supplied to the induction coil 110 by the inverter circuit 108 and provides a current signal 118 to controller 114. The current sensor signal 118 is a signal that is representative of the current flowing through the induction coil 110 derived from one of a plurality of possible devices. For example, the current sensor 117 may include a current transformer, a current shunt monitor, a Hall-Effect sensor, or any suitable current sensing device.

A temperature sensor 119 senses a temperature of a surface of the cookware 112 and provides a temperature signal 120 to the controller 114. The temperature signal 120 is a signal that is representative of a temperature of the surface of the cookware 112 in contact with a sensor contact 122. It is noted that the sensor contact 122 may be a direct contact point, or may be a protected or covered contact point where a portion of a temperature sensor is covered by a protective layer of metal such as aluminum.

According to at least one example embodiment, the temperature sensor 119 is a thermistor or a thermocouple. In some example embodiments, the sensor contact 122 is a spring loaded contact that directly contacts a portion of at least one surface of the cookware 112. The sensor contact 122 may also be mechanically actuated, may be flush with a surface of the induction cooktop of the system 100, and/or may be biased upward by an elastomeric member. Other forms of temperature sensors and contact points may be applicable to example embodiments of the present disclosure. The temperature sensor 119 may also be omitted in some implementations, with precision cooking being provided through determination of cookware material composition alone.

Controller 114 uses the inputs from the user interface 116, the current sensor signal 118 from current sensor 117, and/or the temperature signal 120 from temperature sensor 119 to control energization of the induction coil 110. For example, the controller 114 can use the current sensor signal 118 to sense or detect the presence of the cookware 112 on the induction coil 110, determine a material composition of the cookware 112, implement a temperature offset to the temperature signal 120 based on the material composition when heating the detected cookware 112, and determine the appropriate switching frequency to achieve the output power corresponding to the user selected power setting and/or increase cooking precision.

According to one example, the controller 114 is operative to control the frequency of a power signal generated by inverter module 108 to operate the induction coil 110 at the power level corresponding to the setting selected by the user via user interface 116. The controller 114 monitors the current sensor signal 118 and processes the current sensor signal 118 to determine the presence of the cookware 112 on the induction coil 110 as well as a material composition of the cookware 112. Based on the determined material composition, or lack of determination thereof, the controller 114 is configured to control power to the induction coil 110, which can include turning the power off if no compatible cookware is detected.

The current sensor signal 118 is sampled repetitively during each full switching cycle. The collection of sampled values of current sensor signal 118 over a switching cycle comprises a current signature, which is captured and analyzed by the controller 114 to determine a coil current, a phase shift, and line current through the induction coil 110 and/or system 100.

Figure 2:
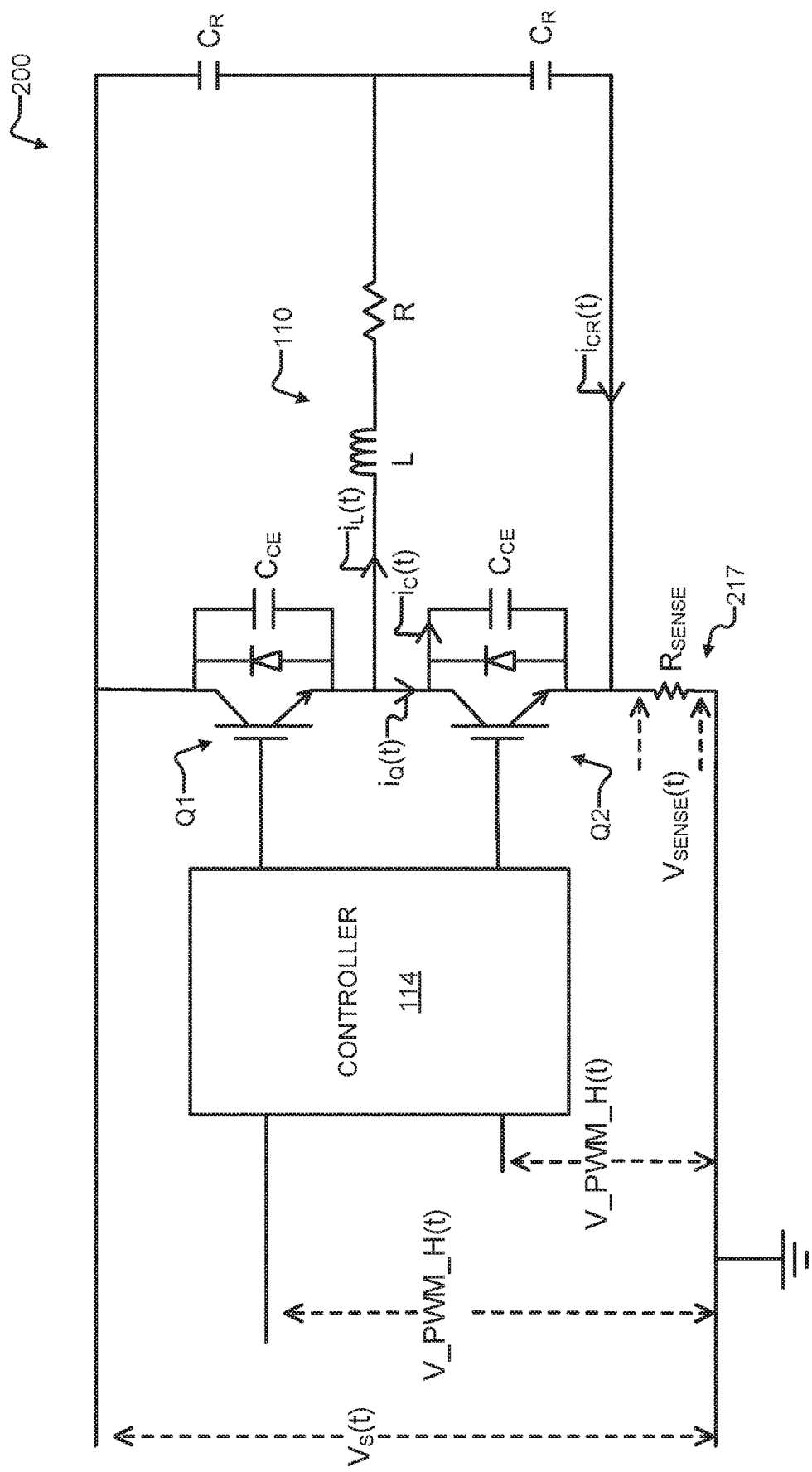
FIG. 2 is a schematic of an implementation of the inverter module and current sensor of the induction heating system of FIG. 1.

FIG. 2 is a schematic of an implementation of the inverter module and current sensor of the induction heating system of FIG. 1. As shown in FIG. 2 the induction heating system 200 includes a current shunt monitor 217 arranged to sense current in the induction coil 110. The current shunt monitor 217 includes a shunt resistor $R_S$ and a capacitor $C_F$. It is noted that other current shunt monitors may also be applicable.

As also shown, inverter module 108 is represented as a half-bridge series resonant converter circuit comprising switching devices Q1 and Q2, and capacitors $C_{CE}$ and $C_R$, which provide alternating current power signal to the induction coil 110 by the controlled switching of the direct voltage provided from the rectification circuit 104. The controller 114 controls the switching of Q1 and Q2 using one or more pulse-width modulated signals. In one embodiment, the switching devices Q1 and Q2 are Insulated-Gate Bipolar Transistors ("IGBT"). In alternate embodiments, any suitable switching devices can be used, including Metal-Oxide Semiconductor Field Effect Transistors and/or any other suitable devices.

Snubber capacitors $C_{CE}$ and resonant capacitors $C_R$ are connected between a positive power terminal and a negative power terminal to successively resonate with the induction coil 110. The induction coil 110 is connected between the switching devices Q1, Q2 and induces an eddy current in a vessel 112 located on or near the induction coil 110. The eddy current heats the vessel 112.

In one embodiment, this switching of switching devices Q1 and Q2 occurs at a switching frequency in a range between approximately 20 kilohertz to 50 kilohertz. When switching device Q1 is turned on, and switching device Q2 is turned off, the resonance capacitor $C_R$, the induction coil 110 and cookware 112 form a resonant circuit. When the switching device Q1 is turned off, and switching device Q2 is turned on, the resonant capacitor $C_R$, the induction coil 110, and the cookware 112 form a resonant circuit. Current shunt monitor 217 provides a sensor signal 118 to controller 114.

Accordingly, the induction coil 110 of the induction cooktop can be arranged as a resonant tank circuit with a shunt resistor $R_S$. Thus obtaining the peak induction coil current, the smoothed input line current, and the phase shift noted above can include sensing a peak induction coil current, a smoothed input line current, and a phase shift via the shunt resistor $R_S$.

By examining the current sensor signal 118, the induction heating system 200 can identify the presence, or lack thereof, of cookware 112 over the induction coil 110. Furthermore, by obtaining a peak induction coil current, a smoothed input line current, and a phase shift of current flowing in the induction coil, and comparing the same to a set of predetermined ranges, candidate material compositions representative of the cookware 112 is possible. Thereafter, the actual material composition of the cookware 112 can be determined as described more fully below with reference to FIGS. 3-5.

As described briefly above, the system 100 may also use current sensing circuitry to facilitate cookware detection, current detection, and phase detection. Optionally, temperature sensors may also be used to aid in precision cooking based on the material composition of cookware, after detection. Using the material composition, a temperature offset may be implemented that more accurately reflects a temperature of a surface of the detected cookware. Hereinafter, operational characteristics of the system 100 are described in detail.

Figure 3:
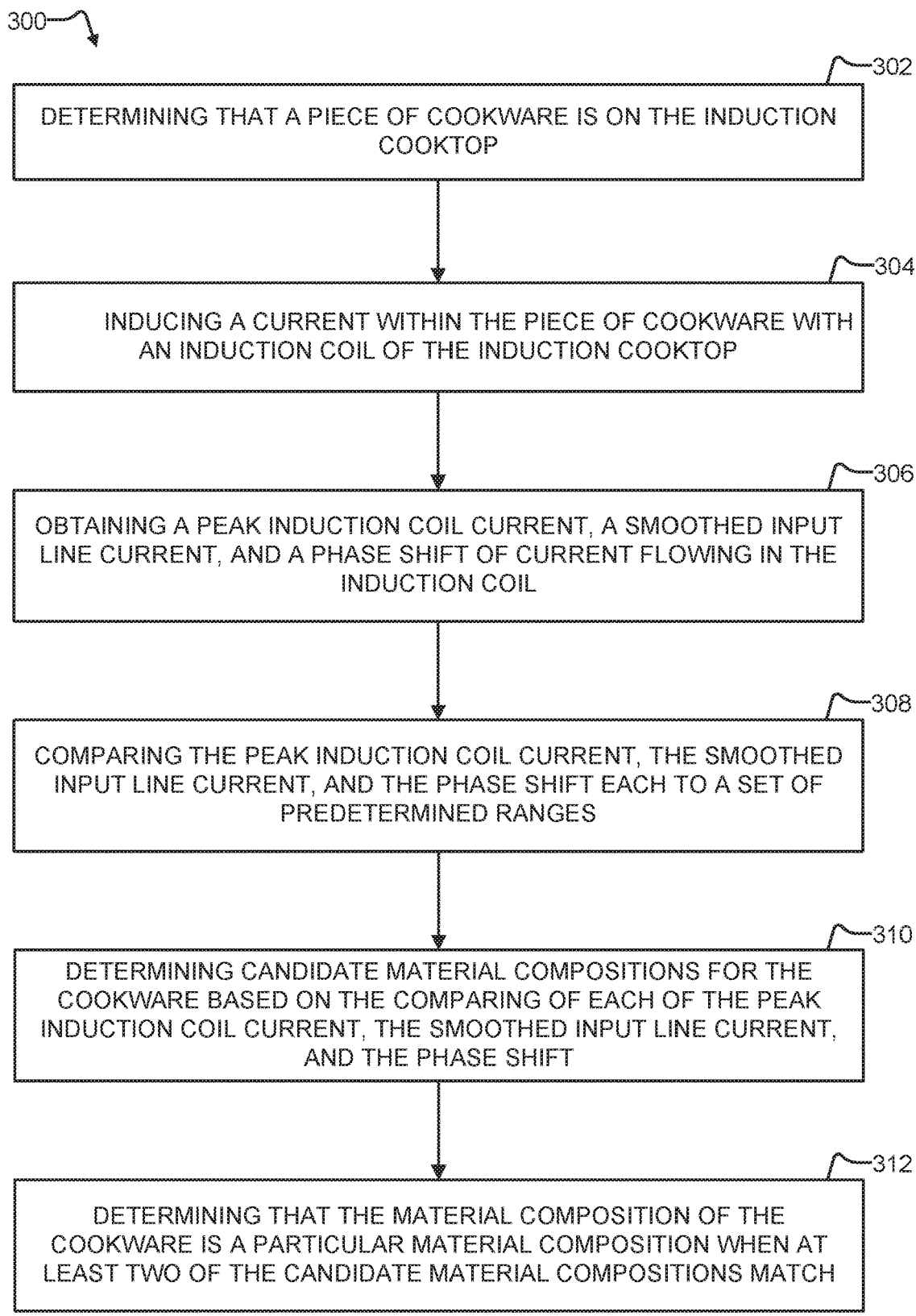
FIG. 3 is a flowchart of a method of determining material composition of cookware on an induction cooktop, according to example embodiments of the present disclosure.
Figure 4:
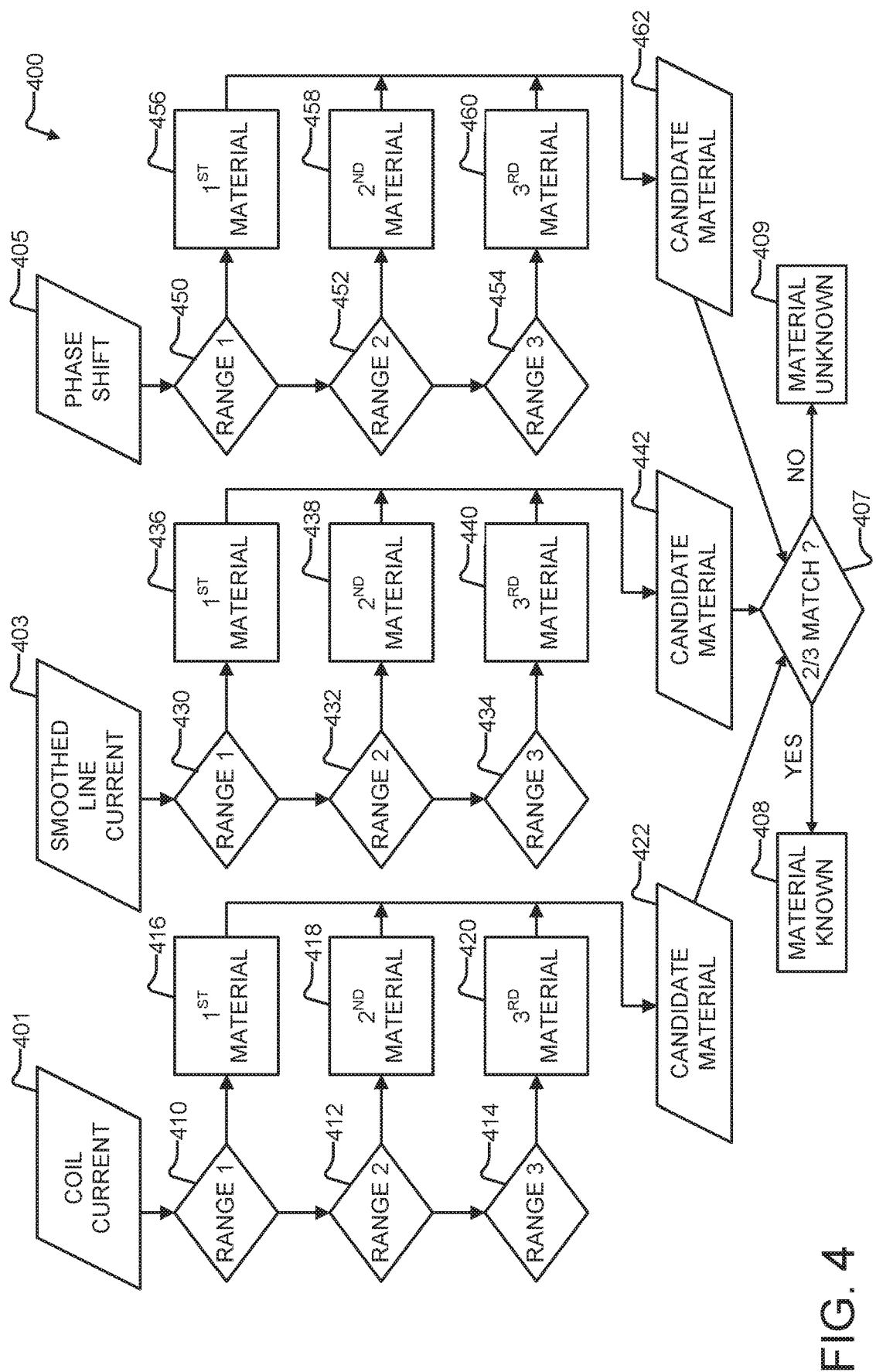
FIG. 4 is a data processing diagram of the method of FIG. 3.

FIG. 3 is a flowchart of a method 300 of determining material composition of cookware on an induction cooktop, according to example embodiments of the present disclosure. Additionally, FIG. 4 is a data processing diagram 400 of the method 300 of FIG. 3.

The method 300 can include determining that a piece of cookware is on the induction cooktop, at block 302. For example, the system 100 can analyze current signal 118 to determine the presence of cookware or other compatible metal placed upon or in range of the induction coil 110. Determining the presence of the cookware may include examining the current signal 118 to determine if inductive coupling has occurred between the induction coil 110 and cookware 112. Determining the presence of the cookware may also include examining the current signal 118 to determine if spikes or other signatures are evident. Other forms of determining are also applicable, and are considered to be within the scope of this disclosure.

The method 300 can further include inducing a current within the piece of cookware 112 with an induction coil 110 of the induction cooktop, at block 304. For example, the control 114 may signal the inverter module 108 or switching devices Q1 and Q2 to supply current to the induction coil 110. As the amplitude of the current supplied changes based on the switching of the switching devices Q1 and Q2, currents are induced in the cookware 112.

The method 300 can also include obtaining a peak induction coil current, a smoothed input line current, and a phase shift of current flowing in the induction coil, at block 306. For example, the controller 114 may sample the current signal 118 and/or the shunt resistor $R_S$ to sense the peak induction coil current, the smoothed input line current, and the phase shift. The sensed values may then be processed by the controller 114 to determine a material composition of the cookware 112, as described below.

The method 300 can also include comparing the peak induction coil current, the smoothed input line current, and the phase shift each to a set of predetermined ranges, at block 306. For example, as illustrated in FIG. 4, peak induction coil current 401, the smoothed input line current 403, and the phase shift 405 are sensed or obtained by the controller 114. Thereafter, the method 300 can also include determining candidate material compositions 422, 442, and 462 for the cookware based on the comparing of each of the peak induction coil current 401, the smoothed input line current 403, and the phase shift 405, at block 308.

As shown in FIG. 4, the comparing includes comparing the peak induction coil current 401, the smoothed input line current 403, and the phase shift 405 to at least three sets of predetermined ranges of values, RANGE 1, RANGE 2, and RANGE 3. It is noted that each of these ranges may be different, similar, or substantially similar. It is also noted that more or fewer ranges may also be used. Thus, for example, the comparing can also include comparing at least two of the peak induction current 401, the smoothed input line current 403, and/or the phase shift 405, to at least two sets of predetermined ranges. In this circumstance, any two of the induction current 401, the smoothed input line current 403, and/or the phase shift 405 may be chosen for the comparison to an associated set of predetermined ranges.

For example, RANGE 1, RANGE 2, and RANGE 3 for coil current 401 may include ranges 410, 412, and 414. Range 410 may correspond to $1^{ST}$ material composition 416. Range 412 may correspond to $2^{ND}$ material composition 418. Finally, range 414 may correspond to $3^{RD}$ material composition 420.

Similarly, RANGE 1, RANGE 2, and RANGE 3 for smoothed line current 403 may include ranges 430, 432, and 434. Range 430 may correspond to $1^{ST}$ material composition 436. Range 432 may correspond to $2^{ND}$ material composition 438. Finally, range 434 may correspond to $3^{RD}$ material composition 440.

Moreover, RANGE 1, RANGE 2, and RANGE 3 for phase 405 may include ranges 450, 452, and 454. Range 450 may correspond to $1^{ST}$ material composition 456. Range 452 may correspond to $2^{ND}$ material composition 458. Finally, range 454 may correspond to $3^{RD}$ material composition 460.

Generally, each of the sets of predetermined ranges includes empirically measured ranges for a plurality of material compositions of cookware. For example, ranges of coil current, smoothed line current, and phase shift may be measured repeatedly for each of the $1^{ST}$, $2^{ND}$, and $3^{RD}$ material compositions. These ranges may then be input as blocks 410, 412, 414, 430, 432, 434, 450, 452, and 454.

The candidate material compositions for these ranges can include stainless steel, cast iron, and enamel-coated cast iron. However, more or fewer material compositions may also be measured empirically and included in methods such as method 300. For example, multiple stainless steel alloys may be included, different thicknesses or coatings for cast iron may be included, and other cookware may also be included.

Turning back to FIG. 3, the method 300 can also include determining that the material composition of the cookware is a particular material composition when at least two of the candidate material compositions match, at block 312. For example, as shown in FIG. 4, each of the candidate material compositions 422, 442, and 462 may be compared at block 407. If at least two of the candidate materials match, the material composition may be known, as shown at block 408. Alternatively, if all of the candidate material compositions do not match, the material composition may not be known, as shown at block 409. Thus, the method 300 can also include determining that the material composition of the cookware 112 is of unknown magnetic composition when all of the candidate material compositions 422, 442, and 462 do not match. In this circumstance, a default temperature and/or cooking profile may be used.

As described above, the comparing of block 306 includes comparing the peak induction coil current 401, the smoothed input line current 403, and the phase shift 405 to at least three sets of predetermined ranges of values, RANGE 1, RANGE 2, and RANGE 3. It is noted that each of these ranges may be different, similar, or substantially similar. Furthermore, a fourth range, RANGE 4 (not illustrated) may be included for comparison in alternate embodiments.

The fourth range may include measurements indicating that there are no matches in RANGE 1, RANGE 2, and RANGE 3. Accordingly, an unknown material decision may then be based on: 1) When all three measurements indicate different materials; 2) When at least two measurements indicate "unknown material"; or, 3) When one measurement indicates a first material, another measurement indicates a different material, and the third measurement indicates "unknown material." It is noted that this alternative is compatible with the method 300 and 400 as illustrated.

Furthermore, although particularly described as being based on direct comparisons to empirically measured ranges, other algorithms may be used to determine candidate material compositions. For example, according to at least one example embodiment, determining candidate material compositions for the cookware 112 can include classifying the cookware 112 as a candidate material based on a material composition class most common among k nearest neighbors of a database of values for the peak induction coil current 401, the smoothed input line current 403, and the phase shift 405. This may be termed use of a K nearest neighbor algorithm (KNN). Use of the KNN algorithm may be facilitated in method 300. Alternatively, a simplified method 500 may be implemented.

Figure 5:
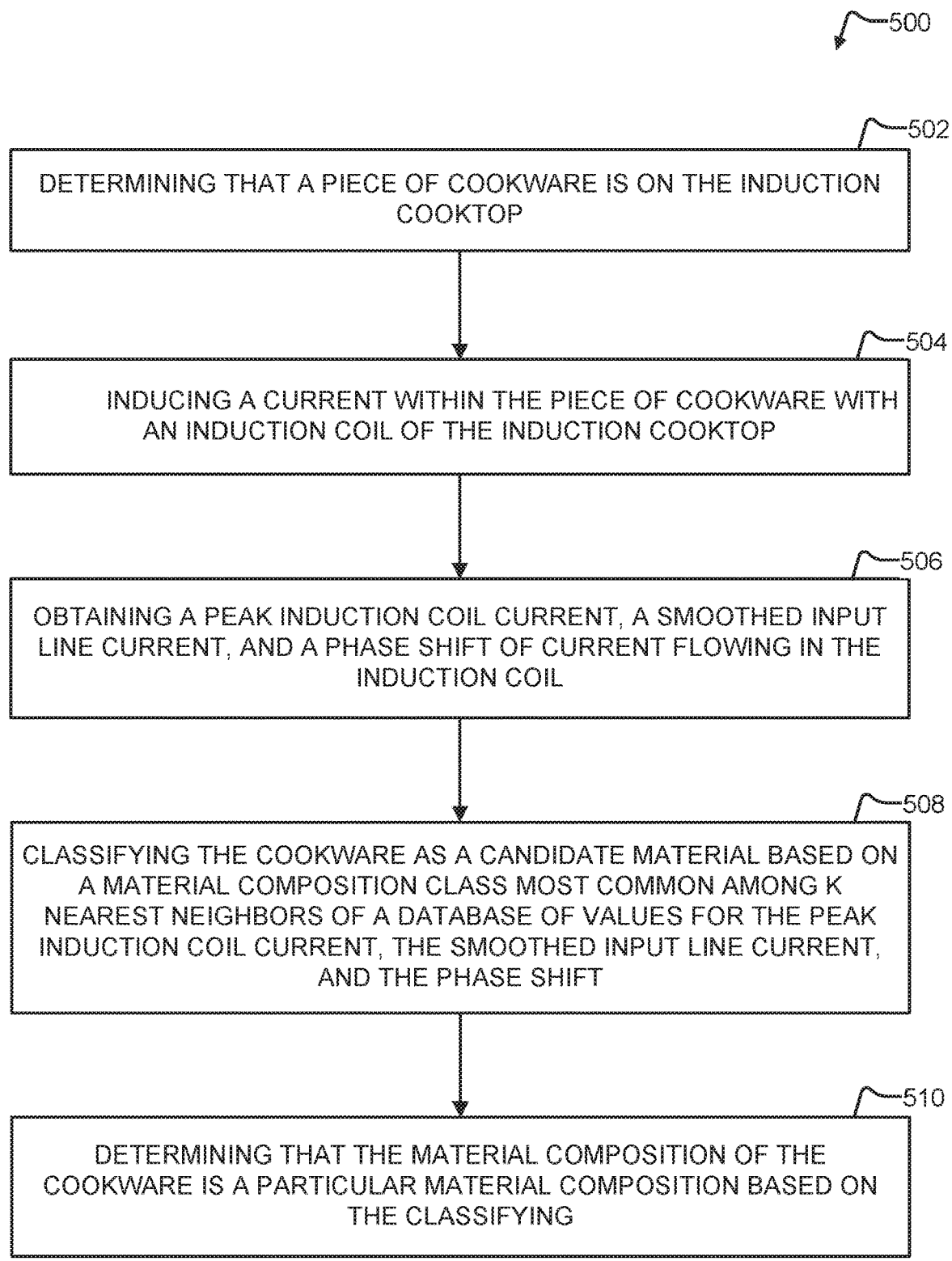
FIG. 5 is a flowchart of a method of determining material composition of cookware on an induction cooktop, according to example embodiments of the present disclosure.

FIG. 5 is a flowchart of a method 500 of determining material composition of cookware on an induction cooktop, according to example embodiments of the present disclosure. The method 500 may include determining that a piece of cookware is on the induction cooktop, at block 502; inducing a current within the piece of cookware with an induction coil of the induction cooktop, at block 504; and obtaining a peak induction coil current, a smoothed input line current, and a phase shift of current flowing in the induction coil, at block 506. It is noted that blocks 502, 504, and 506 are substantially similar to blocks 302, 304, and 306. Therefore, detailed description of each is omitted herein for the sake of brevity.

The method 500 may further include classifying the cookware as a candidate material based on a material composition class most common among k nearest neighbors of a database of values for the peak induction coil current, the smoothed input line current, and the phase shift, at block 508. The database of values includes empirically measured data points for a plurality of material compositions of cookware, similar to the empirically measured data described above. Furthermore, block 508 may be a direct implementation of the KNN algorithm described above.

According to one example embodiment, the database includes more than 60 data points to accurately determine material composition of cookware. More or fewer data points may be used in any desired implementation. Furthermore, increased or decreased sensitivity may be implemented by altering a number of neighbors required for a positive candidate match.

Thereafter, the method 500 includes determining that the material composition of the cookware is a particular material composition based on the classifying, at block 510. For example, an output of the KNN algorithm may be used as the material composition of the cookware 112.

Upon implementation of either of methods 300 or 500 to determine material composition of the cookware 112, and based on the actual material composition determined, accurate and precise cooking may be implemented using the temperature sensor 119. Temperature feedback provided by the sensor 119 may be offset depending upon the material composition of the cookware 112, thereby more accurately reflecting the actual temperature of the cookware.

For example, stainless steel cookware may have a smooth surface that makes good contact with contact point 122. In this regard, the temperature offset may be relatively small. However, cast iron may have a porous and rough surface that does not make good contact with contact point 122. Accordingly, the temperature offset may be larger than that for stainless steel. It follows then that enamel-coated cast iron may have a smooth surface but poor surface conductivity. It is therefore apparent that the temperature offset may be larger than that for regular cast iron.

Upon implementation of the temperature offset, more precise control over the actual temperature of the cookware 112 may be possible. Therefore, the user requested power settings input through user interface 116 may be more accurately implemented in the actual cookware 112, resulting in more even heating at a value closer to that requested by a user.

Accordingly, example embodiments of the present disclosure benefit consumers by providing more precise cooking, save energy by providing for accurate heating profiles based on material composition of cookware, conserve resources for the controller, and provide for accurate temperature feedback to reduce the chance of damaging cookware due to overheating or overly aggressive heating profiles.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method of determining material composition of cookware on an induction cooktop, comprising:
   determining that a piece of cookware is on the induction cooktop;
   inducing a current within the piece of cookware with an induction coil of the induction cooktop;
   obtaining a peak induction coil current, a smoothed input line current, and a phase shift of current flowing in the induction coil;
   comparing the peak induction coil current, the smoothed input line current, and the phase shift each to a set of predetermined ranges; and
   determining candidate material compositions for the cookware based on the comparing of each of the peak induction coil current, the smoothed input line current, and the phase shift.

2. The method of claim 1, wherein the induction coil of the induction cooktop is arranged as a resonant tank circuit with a shunt resistor, and wherein obtaining the peak induction coil current, the smoothed input line current, and the phase shift comprises:
   sensing the peak induction coil current, the smoothed input line current, and the phase shift via the shunt resistor.

3. The method of claim 1, wherein the set of predetermined ranges include empirically measured ranges for a plurality of material compositions of cookware, and wherein the candidate material compositions comprise stainless steel, cast iron, and enamel-coated cast iron.

4. The method of claim 1, wherein determining candidate material compositions for the cookware comprises:
   comparing the peak induction coil current, the smoothed input line current, and the phase shift to at least two sets of predetermined ranges of values.

5. The method of claim 1, wherein determining candidate material compositions for the cookware comprises:
   classifying the cookware as a candidate material based on a material composition class most common among k nearest neighbors of a database of values for the peak induction coil current, the smoothed input line current, and the phase shift.

6. The method of claim 1, further comprising:
   determining that the material composition of the cookware is a particular material composition when at least two of the candidate material compositions match.

7. The method of claim 1, further comprising:
   determining that the material composition of the cookware is of unknown magnetic composition when all of the candidate material compositions do not match.

8. An induction cooktop, comprising:
   an induction coil;
   a switching device configured to operate the induction coil; and
   a controller configured to operate the switching device, wherein the controller is configured to perform operations, the operations comprising:
      determining that a piece of cookware is on the induction cooktop;
      inducing a current within the piece of cookware with an induction coil of the induction cooktop;
      obtaining a peak induction coil current, a smoothed input line current, and a phase shift of current flowing in the induction coil;
      comparing the peak induction coil current, the smoothed input line current, and the phase shift each to a set of predetermined ranges; and
      determining candidate material compositions for the cookware based on the comparing of each of the peak induction coil current, the smoothed input line current, and the phase shift.

9. The induction cooktop of claim 8, wherein the induction coil is arranged as a resonant tank circuit with a shunt resistor, and wherein obtaining the peak induction coil current, the smoothed input line current, and the phase shift comprises:
   sensing the peak induction coil current, the smoothed input line current, and the phase shift via the shunt resistor.

10. The induction cooktop of claim 8, wherein the set of predetermined ranges include empirically measured ranges for a plurality of material compositions of cookware.

11. The induction cooktop of claim 8, wherein the candidate material compositions comprise stainless steel, cast iron, and enamel-coated cast iron.

12. The induction cooktop of claim 8, wherein determining candidate material compositions for the cookware comprises:
   comparing the peak induction coil current, the smoothed input line current, and the phase shift to at least two sets of predetermined ranges of values.

13. The induction cooktop of claim 8, wherein determining candidate material compositions for the cookware comprises:
   classifying the cookware as a candidate material based on a material composition class most common among k nearest neighbors of a database of values for the peak induction coil current, the smoothed input line current, and the phase shift.

14. The induction cooktop of claim 8, wherein the controller is further configured to:
  determine that the material composition of the cookware is a particular material composition when at least two of the candidate material compositions match; and
  determine that the material composition of the cookware is of unknown magnetic composition when all of the candidate material compositions do not match.

15. The induction cooktop of claim 8, further comprising at least one temperature sensor configured to determine a temperature of at least one surface of cookware.

16. The induction cooktop of claim 15, wherein the at least one temperature sensor includes a spring-loaded sensor contact configured to contact the at least one surface of the cookware.

17. A method of determining material composition of cookware on an induction cooktop, comprising:
  determining that a piece of cookware is on the induction cooktop;
  inducing a current within the piece of cookware with an induction coil of the induction cooktop;
  obtaining a peak induction coil current, a smoothed input line current, and a phase shift of current flowing in the induction coil;
  classifying the cookware as a candidate material based on a material composition class most common among k nearest neighbors of a database of values for the peak induction coil current, the smoothed input line current, and the phase shift; and
  determining that the material composition of the cookware is a particular material composition based on the classifying.

18. The method of claim 17, wherein the induction coil is arranged as a resonant tank circuit with a shunt resistor, and wherein obtaining the peak induction coil current, the smoothed input line current, and the phase shift comprises:
  sensing the peak induction coil current, the smoothed input line current, and the phase shift via the shunt resistor.

19. The method of claim 17, wherein the material compositions comprise stainless steel, cast iron, and enamel-coated cast iron.

20. The method of claim 17, wherein the database of values includes empirically measured data points for a plurality of material compositions of cookware.

* * * * *